United States Patent [19]
Han

[11] Patent Number: 6,121,050
[45] Date of Patent: Sep. 19, 2000

[54] ANALYTE DETECTION SYSTEMS

[76] Inventor: Chi-Neng Arthur Han, 3711 Hamilton St., 3rd Floor, Philadelphia, Pa. 19104

[21] Appl. No.: 08/920,822

[22] Filed: Aug. 29, 1997

[51] Int. Cl.[7] .......................... G01N 33/50; G01N 31/22; G01N 33/52

[52] U.S. Cl. ............................... 436/95; 436/46; 436/93; 436/94; 436/166; 436/169; 436/172; 422/56; 422/82.08; 422/82.09

[58] Field of Search ................... 436/46, 93–95, 436/164, 166, 169, 172; 422/56, 82.05, 82.08, 82.09

[56] References Cited

U.S. PATENT DOCUMENTS

| | | |
|---|---|---|
| 4,427,889 | 1/1984 | Müller ...................................... 250/339 |
| 4,637,978 | 1/1987 | Dappen . |
| 4,673,635 | 6/1987 | Yamanishi et al. . |
| 4,772,561 | 9/1988 | Genshaw ................................. 436/169 |
| 4,876,207 | 10/1989 | Mack, II et al. . |
| 4,935,346 | 6/1990 | Phillips et al. . |
| 5,049,487 | 9/1991 | Phillips et al. . |
| 5,059,394 | 10/1991 | Phillips et al. . |
| 5,174,963 | 12/1992 | Fuller et al. . |
| 5,179,005 | 1/1993 | Phillips et al. . |
| 5,183,741 | 2/1993 | Arai et al. . |
| 5,185,247 | 2/1993 | Ismail et al. . |
| 5,204,242 | 4/1993 | Junius-Comer et al. . |
| 5,212,060 | 5/1993 | Maddox ................................... 435/7.1 |
| 5,304,467 | 4/1994 | Sakamoto et al. . |
| 5,304,468 | 4/1994 | Phillips et al. . |
| 5,306,623 | 4/1994 | Kiser et al. . |
| 5,362,633 | 11/1994 | Pugia . |
| 5,382,523 | 1/1995 | Hoenes et al. . |
| 5,389,524 | 2/1995 | Larsen et al. . |
| 5,424,194 | 6/1995 | Otagiri et al. . |
| 5,426,032 | 6/1995 | Phillips et al. . |
| 5,452,716 | 9/1995 | Clift ........................................ 128/633 |
| 5,453,360 | 9/1995 | Yu . |
| 5,520,883 | 5/1996 | Charlton et al. . |
| 5,527,684 | 6/1996 | Mabile et al. . |
| 5,532,138 | 7/1996 | Singh et al. . |

OTHER PUBLICATIONS

S. Ebel *CLB, Chem. Labor Betr.* 1988, 39, 116 & 118.
H–W Gao *Shanghai Huanjing Kexue* 1993, 12, 36–37.
S. Brewer "Solving Problems in Analytical Chemistry" John Wiley & Sons, Inc, New York 1980 pp. 256–285.
N.F. Jaffery et al, *J. Pharmacol. Methods* 1983, 9, 33–39.
Z. Zhang et al. *Fenxi Huaxue* 1985, 13, 262–265.
J.L. Xu et al. *Acta Pharmaceut. Sinica* 1990, 25, 626–631.
D. Zhang et al. *Fenxi Huaxue* 1991, 19, 1068–1071.
C. Zhao et al. *Yejin Feuxi* 1993, 13, 12–14.
Z. Nan et al. *Analyst* 1993, 118, 1077–1080.
H, W. Gao *Talanta* 1995 42, 891–895.

*Primary Examiner*—Arlen Soderquist
*Attorney, Agent, or Firm*—Hoffman & Baron, LLP

[57] ABSTRACT

The present invention is directed to an improved analyte systems which are able to compensate for interfering signals and to provide accurate detection and/or quantification of analytes in a sample. In particular, the invention describes new methods, systems, and devices for indirectly determining the presence of one or more analytes in a multi-component medium.

33 Claims, 3 Drawing Sheets

ANALYTE DETECTION SYSTEMS

FIELD OF INVENTION

This invention relates generally to analyte detection systems, and in particular to methods, systems and devices for indirectly determining the presence of one or more analytes in a multi-component medium. The invention is particularly useful in detecting the presence and/or concentration of glucose in a blood sample.

BACKGROUND OF THE INVENTION

The detection and quantification of chemical and biochemical components in aqueous fluids, in particular biological fluids, such as, whole blood and urine and biological fluid derivatives, such as, blood serum and blood plasma, is of ever-increasing importance. Important applications exist in medial diagnosis and treatment and in the quantification of exposure to therapeutic drugs, intoxicants, hazardous chemicals and the like. In some instances, the amount of materials being determined are either so small or so difficult to precisely determine that the apparatus employed is complicated and useful only to skilled laboratory personnel. In this case, the results are generally not available for hours or days after sampling. These apparati are not for suitable for operation by patients who often need to perform such tests routinely, quickly and reproducibly outside of a laboratory setting with rapid or immediate information display.

Devices and methods are generally known for detecting analytes, such as glucose, in a blood sample. For example, one common medical test is the measurement of blood glucose levels by diabetics. Current diabetes maintenance programs encourage patients to measure their blood glucose level from two to seven times a day, depending on the nature and severity of the disease. Based on the observed pattern in the measured glucose levels, the patient and physician make adjustments in diet, exercise and insulin intake to better manage the disease. Clearly, the accuracy and immediacy of the results of such tests is paramount.

Thus, the art is replete with examples of methods for detecting glucose in a blood sample. For example, U.S. Pat. No. 5,179,005 to Phillips et al. discloses a method for determining the presence of an analyte in a fluid. In this method, a MBTH-DMAB (3-methyl-2-benzothiazolinone hydrazone hydrochloride and 3-dimethylaminobenzoic acid) dye forms a chromophore when reacted with an analyte such as, for example, glucose. This dye absorbs at approximately 635 nm but does not absorb to any significant extent at 700 nm. Because blood contains background materials which absorb at both 635 nm and 700 nm, this method requires that a relationship between absorbants at 635 nm and 700 nm due to blood contaminants be determined by measuring the absorbance of blood samples with 0 mg/dl glucose over a wide range of blood colors. Such a color range was constructed by varying the hematocrit of the blood which results in substantially linear relationships. From these relationships, contaminating absorbance readings at 700 nm are normalized to the equivalent contaminating absorbant readings at 635 nm. This normalization was expressed as $K/S-15n=(K/S-15\cdot1.54)-0.133$. Using this relationship, as well as others, contaminating absorbencies at 635 nm were accounted for and subtracted out to give a true glucose concentration. Such a method is limited, however, because the selected dye must absorb at a wavelength that is different from the wavelength at which red blood cells absorb. Furthermore, the need to construct a standard for the background materials in blood is time consuming and expensive.

A similar test for glucose is disclosed by U.S. Pat. No. 5,426,032 to Phillips et al. which describes a no-wipe whole blood glucose test strip. This test strip is adapted for use in a reflectance reading apparatus that is capable of measuring reflectance at two different wavelengths. This patent is similar to Phillips' earlier issued '005 patent because a background absorbance reading must be taken at 700 nm while the reflectance of the chromophore is read at 635 nm. Thus, in the '032 patent when measuring analytes contained in whole blood, readings are taken at two different wavelengths. The reading at one wavelength, e.g. 700 nm, is used to subtract out the background interference caused by, for example, hematocrit, blood oxygenation, and other variables which may affect the result. The method of this patent, however, is limited in that the signal-producing reagent must be absorbed at a wavelength other than a wavelength at which the assay medium substantially absorbs. Furthermore, this method is unable to correct for contaminants and/or other analytes which absorb at the chromophore's wavelength, i.e., 635 nm, and at the same time the chromophore produced by the analyte also absorbs at a second wavelength, i.e., 700 nm.

In a slightly different approach to correcting for contaminating signals during analyte detection in a sample, U.S. Pat. No. 5,453,360 to Yu describes an oxidative coupling dye for photometric quantitative analysis of such analytes. In particular, a dye couple is described which includes 3-methyl-2-benzothiazolinone hydrazone (NBTH) and 8-aniline-1-naphthalenesulfonate (ANS). This dye couple is used as an indicator in a reaction cascade that produces a strong oxidizing agent, such as, hydrogen peroxide. This strong oxidizing agent then reacts with the dye couple to produce a blue dye reaction product. The NBTH-ANS dye couple exhibits strong and flat spectral absorption at about 600 to 650 nm. This region of absorbance is free of blood color interference. Accordingly, glucose and other analytes that react with an oxidase enzyme to produce the above-described strong oxidizing agent can be accurately measured without much optic calibration. This patent is limited because the dye couple must absorb in an area of the reflectance spectrum between 600 and 650 nm which is outside the region of blood color interference or the dye couple must be used in the absence of red blood cells so that it would not to be subject to interference by the color of the blood. More generally, this patent suffers from the drawback that unknown components in a sample which happen to absorb at the detection wavelength will cause the analyte measurements to be over-estimated.

Similarly, U.S. Pat. No. 5,389,524 to Larsen et al. describes a method and an apparatus for quantitatively monitoring a chemical component dissolved in a liquid medium. This patent describes taking two measurements of a system at the same wavelength. The absorbance of a colored reaction product is determined by subtracting an end-point absorbance from a background absorbance. Thus, this patent takes two absorbance measurements at the same wavelength and is susceptible to erroneous results if one or more analytes or interfering substances happen to absorb at the same wavelength that the two absorbance measurements are taken.

Non-glucose analyte detection systems are also well known in the art. For example, U.S. Pat. No. 5,204,242 to Junius-Comer describes the use of a substituted phenol with high stability and low non-specific reactivity as a coupling component used in a colormetric process for detecting oxidative coupling reactions, such as the determination of enzymatic creatinine levels. In this method, a reference measurement is made at 700 nm before the reaction starts; while the extinction increase is measured at 546 nm between the sixth and tenth minute of reaction. This method is limited by its assumption that no interfering component absorbs at the detection wavelength, i.e., 546 nm.

It is also known in the art to use fluorescent or other detection schemes for determining the presence and/or quantity of an analyte in a sample. For example, U.S. Pat. No. 5,527,684 to Mabile et al. describes a method of measuring the luminescence emitted in a luminescent assay. This method includes forming a reaction mixture by contacting a sample with an internal reference compound that emits at a first wavelength and a tracer compound that emits at a second wavelength. The sample is then irradiated at a single excitation wavelength. The tracer is detected by measuring the emitted luminescence at the second wavelength. The internal reference is detected by measuring the emitted luminescence at the first wavelength. Using the luminescence emitted at the first wavelength by the internal reference, a correction is made to the luminescence emitted at the second wavelength by the tracer. In this way, the analyte in question can be quantified or detected.

In summary, the prior art methods cited above all suffer from the drawback that they are susceptible to overestimating and/or providing false positive results if a contaminating component of a sample happens to absorb at the detection wavelength. Thus, there is a need for an improved analyte detection system which is able to compensate for interfering absorbencies and to provide accurate detection and/or quantification of analytes in a sample. In particular, there is a need for quick, cost-effective, accurate and easy-to-use methods and systems for indirectly determining the presence and/or quantity of one or more analytes in a system. The present invention is directed to meeting these and other needs.

SUMMARY OF THE INVENTION

In one embodiment of the present invention, there is provided method for indirectly determining the presence of one or more analytes in a multi-component medium. This method includes reacting the multi-component medium with one or more signal-producing reagents to form one or more signal producing molecules which produce characteristic spectra in response to one or more stimuli in that the ratios of these signals produced from the same molecules are constants and are characteristic of the molecule. A stimulus or stimuli is then provided or self-produced by the signal producing molecule for exciting the multi-component medium whereby the number of stimuli provided or self-produced is equal to or greater than the sum of the number of the analytes and any interfering components in the multi-component medium, provided that when there is more than one analyte or interfering component in the multi-component medium that the stimuli provided or self-produced to correct the interference are different from a stimulus for measuring the analyte, and the interference-correcting signals at these stimuli do not overlap each other. This method further includes detecting at least a first and second signal of one or more analytes generated in response to the stimulus or stimuli. The presence and/or concentration of one or more of the analytes is determined by applying mathematical formulas to at least the first and second signals.

In another embodiment of the present invention, there is provided an analyte detection system for determining the presence and/or concentration of glucose in a blood sample which is in contact with a porous substrate having a blood application surface and an analyte detection surface thereon, wherein the presence and/or concentration of glucose cannot be directly determined. This system includes a means for introducing the blood sample onto the blood application surface of the substrate. The sample is then allowed to migrate through the porous substrate to the analyte detection surface. The detection surface includes a glucose-specific reagent and indicator disposed thereon. A signal producing composition is allowed to form on the analyte detection surface through the reaction of the glucose-specific reagent, the indicator and the glucose present in the blood sample. The sample is then stimulated with one or more stimuli used to correct for interference generated by another analyte or interfering component. The signals produced in response thereto are then detected. Such detection is based on the requirement that the number of interference-correcting stimuli required is equal to or greater than the sum of the number of analytes in the sample and any interfering components therein, provided that the stimuli are different from a stimulus for measuring the glucose, and that these interference-correcting stimuli do not overlap each other. The presence and/or concentration of the glucose is determined by applying mathematical formulas as further described herein to the produced signal(s).

In a further embodiment of the present invention, there is provided a process for detecting one or more analytes in a multi-component system, wherein the ability to directly detect one or more analytes is masked. This process includes forming a signal producing composition by reacting an analyte with a reagent. The system is then excited with one or more stimuli to produce an interference-correcting signal from the signal producing composition, whereby the number of stimuli provided is equal to or greater than the sum of the number of analytes and any interfering components in the multi-component medium, provided that the interference-correcting stimuli are different from a stimulus for measuring the analyte, and that these interference-correcting signals at these stimuli do not overlap each other. The signal or signals are then measured and the presence and/or concentration of one or more of the analytes is determined by applying mathematical formulas to the signal or signals. These mathematical formulas are defined as follows:

$$\text{Concentration of Analyte} = E \cdot Aa$$

wherein E is an extinction coefficient and $Aa=(Aa'-k \cdot Bb')/(1-k \cdot c)$ and wherein Aa is the true value for the analyte, Aa' is a measurable signal produced in response to a single stimulus by the signal producing composition (Aa) and no more than one interfering component (Ba) at the first detection point, Bb' is a measurable signal produced in response to the stimulus by the signal producing composition (Ab) and no more than one interfering component (Bb) at the second detection point, k is a constant and is also the ratio between Bb and Ba, and c is the ratio between Aa and Ab.

In a still further embodiment of the present invention, there is provided a device for detecting the presence and/or concentration of one or more analytes in a blood sample when the analyte cannot be directly detected. This device includes a hydrophilic porous substrate with a blood application surface and an analyte detection surface. The substrate includes a polymeric matrix having pores dispersed throughout the matrix and in communication with the blood application and analyte detection surfaces. The diameter of the pores of the polymeric matrix are sufficiently large to allow red blood cells in the sample to freely migrate between the blood application and analyte detection surfaces.

An analyte-specific reagent and an indicator are dispersed on the analyte detection surface for reacting with the analyte to produce a signal producing composition. When excited, this signal producing composition produces at least two interference-correcting signals at wavelengths ($\lambda_a$) and ($\lambda_b$), respectively to allow for the correction of any interfering signals produced by other analytes or interfering components in the sample. The device also includes excitation means for exciting the sample on the analyte detection surface. These excitation means can be, for example, a laser, a visible light source, etc. Moreover, detection means are also provided for detecting at least two signals. The number of interference-correcting signals produced, however, must be equal to or greater than the sum of the number of the analytes in the blood sample and any interfering components therein, provided that the interference-correcting signals are different from a signal for measuring the analyte, and that the interference-correcting signals at these stimuli do not overlap each other. The device further includes a means for determining the presence and/or concentration of the analyte by applying mathematical formulas to at least the first and second signals. These formulas are defined as follows:

Concentration of Analyte=E·Aa wherein E is an extinction coefficient and Aa=(Aa'-k·Bb')/(1−k·c) and Aa is the true value for the analyte, Aa' is a measurable signal produced at $\lambda_a$ by the signal producing composition (Aa) and no more than one interfering component from the sample (Ba), Bb' is a measurable signal produced at $\lambda_b$ by the signal producing composition (Ab) and no more than one interfering component from the sample (Bb), k is a constant and is the ratio between Bb and Ba, and c is the ratio between Aa and Ab. A display means is also provided for displaying the presence and/or concentration of the analyte.

DETAILED DESCRIPTION OF THE INVENTION

The present invention is directed to a method for indirectly determining the presence of one or more analytes in a multi-component medium, wherein the presence of one or more analytes to be detected are proportional to the magnitude of a signal (Aa) as set forth in more detail hereinbelow. For purposes of the present invention, the use of the term "indirectly" means that the present method is able to detect an analyte whether or not its signal is masked by an interfering contaminant, the color of the sample, or another analyte(s).

For purposes of the present invention, an "analyte" is any composition found in a sample for which it would be useful to detect its presence and/or quantity. More particularly, the analytes of the present invention can be any medically significant composition for which the presence or quantity thereof in a body is important to ascertain. Non-limiting examples of such analytes include glucose, creatinine, cholesterol, uric acid, methanol, ethanol, formaldehyde, glycerol-3-phosphate. In addition, kinetic assays, such as those used to detect or measure enzymes can also be used in accordance with the present invention.

The analyte or analytes of the present invention are detected in a multi-component medium. For purposes of the present invention, "multi-component medium" refers to both aqueous and non-aqueous solutions containing at least one analyte to be detected. The multi-component medium can also contain other analytes or interfering components which may or may not interfere with the detection of the analyte of interest. Preferably, the multi-component medium of the present invention refers to biological fluid samples, including for example, blood, urine, saliva and derivatives thereof. Derivatives of blood include, for example, serum and plasma, as well as, artificial and/or synthetic blood.

In the present invention, the multi-component medium is reacted with one or more signal producing reagents to form one or more signal producing molecules. For purposes of the present invention, the term "signal producing reagents" refers to compositions which react with one or more analytes in a multi-component medium to produce one or more reaction products. These signal producing reagents are selected with reference to the analyte or analytes to be detected, the composition of the multi-component medium and the detection device. The selection of appropriate signal producing reagents is within the knowledge of the skilled artisan given the above-referenced variables.

For purposes of illustration only and not by way of limitation, the signal producing reagents of the present invention can include for example, chromogens, such as 3,3',5,5'-Tetramethylbenzidine and Trinder reagents, glucose oxidase, peroxidase, and oxygen acceptors such as, O-dianisidine, O-toluidine, O-tolidine, benzidine, 2,2'-azinodi-(3-ethylbenzthiazoline sulphonic acid-(6)), 3-methyl-2-benzothiazolinone hydrazone and N,N-dimethylaniline, phenyl and 4-aminophenazone, sulfonated 2,4-dichlorophenol and 4-aminophenazone, 3-methyl-2-benzothiazolinone hydrazone and 3-(dimethylamino) benzoic acid, 2-methoxy-4-allyl phenol and 4-aminoantipyrenedimethylaniline.

Furthermore, the present invention contemplates the use of single or multi-signal-producing reagents, depending on the analyte or analytes to be detected. Moreover, the present invention also contemplates the use of systems of signal producing reagents which work together to produce a signal producing molecule and/or for enhancing the signal produced by such a molecule.

For purposes of the present invention, "signal producing molecule" or "signal producing molecules" refers to the reaction product produced from reacting one or more signal-producing reagents with the multi-component medium. Such signal producing molecules produce a measurable event that is used in the present invention to detect or quantitate the analyte or analytes of interested. This measurable event is typically, for example, a signal which is detectable using conventional methods including, absorbance, voltage, radioactivity, nuclear magnetic resonance, temperature, current and fluorescence. Furthermore, the present invention also encompasses signal producing molecules which produce a measurable response which has a characteristic ratio of signals at different stimuli.

The signal produced by these signal producing reagents may be self-produced or provided in response to one or more stimuli. In either case, these signals usually produce a spectrum which is detectable by one of the methods set forth above. In the present invention, there is a requirement that the number of stimuli provided or self-produced must be equal to or greater than the sum of the number of analytes and any interfering components in the multi-component medium. Thus, in a simple system of glucose and water, where glucose is the analyte to be determined, the number of stimuli must be one or more. In a system where there are two analytes or one analyte and one interfering component, there must be at least two stimuli in order to properly quantitate or detect the analyte of interest. There is no theoretical limit to the number of analytes or interfering components that can be present in the multi-component medium so long as the number of stimuli provided or self-produced is equal to or greater than the sum of the analytes and interfering components therein. For purposes of the present invention, an "interfering component" is any composition present in the multi-component medium which is capable of interfering with the measurement of the analyte of interest.

In the present invention, at least a first and a second signal are detected in response to the signal generated by the signal producing molecules when the stimulus or stimuli are provided to the multi-component medium. These signals are detected using conventional technology, such as for example, spectrophotometers, fluorescence spectrophotometers, voltage detectors, etc. The selection of an appropriate device for detecting such signals is within the knowledge of one skilled in the art with reference to the analytes to be detected, the signal-producing reagents used, the signal producing molecules formed, as well as, the composition of the multi-component medium.

Once a signal is detected, the presence and/or concentration of one or more analytes is determined by applying mathematical formulas to at least the first and second signals produced. These mathematical formulas are defined according to the following formula:

Concentration of Analyte=E·Aa    (Formula I)

wherein E is an extinction coefficient and Aa=(Aa'-k·Bb')/(1-k·c) and Aa is the true value for the analyte Aa' is a measurable signal produced in response to a stimulus by the signal producing molecule (Aa) and no more than one of the interfering components (Ba) at $\lambda_a$, Bb' is a measurable signal produced in response to the stimulus by the signal producing molecule (Ab) and no more than one of the interfering components (Bb) at $\lambda_b$, k is a constant and is a ratio between Bb and Ba, and c is the ratio between Aa and Ab.

Figure 1:
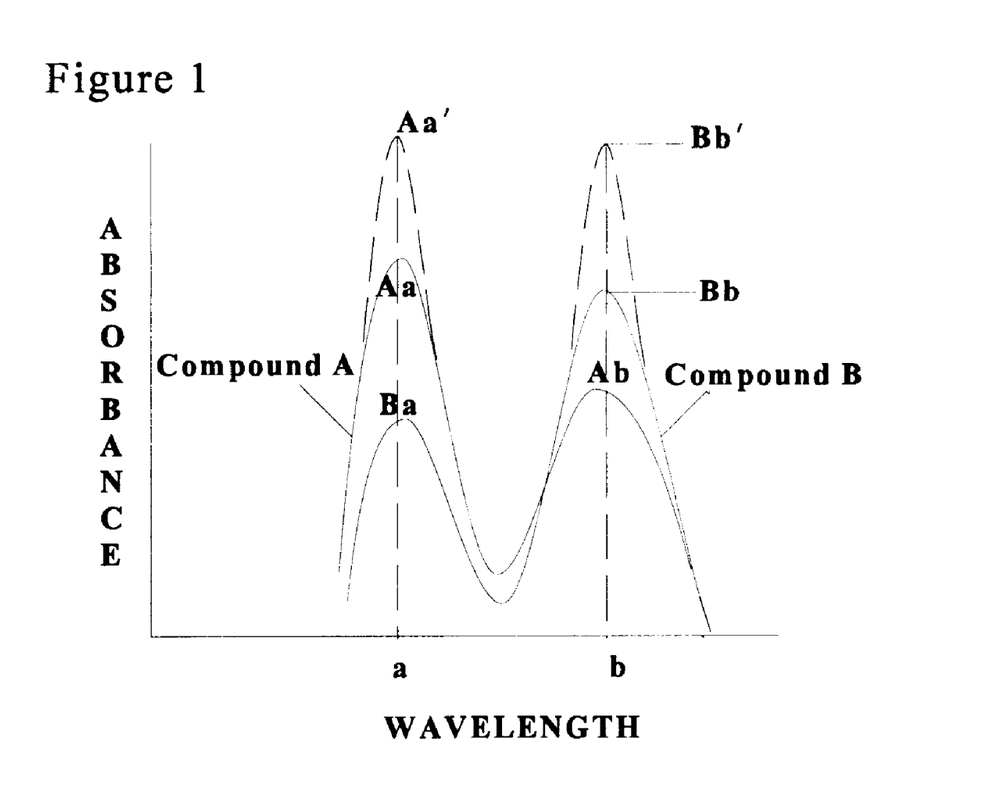
FIG. 1 depicts the absorbance of two compounds at two wavelengths according to the present invention.

With reference to FIG. 1, the present invention includes a signal producing system which reacts with an analyte (Compound A) to produce a signal, such as for example a chromophore, which absorbs at a specific wavelength ($\lambda_a$). The intensity of the absorbance at this wavelength is measured and is then related to the concentration of the analyte. If background or contaminant materials, i.e., other analytes or interfering components, (Compound B) also absorb at the same wavelength as the chromophore, an absorbance measurement is taken at a second wavelength ($\lambda_b$), even if the chromophore also absorbs at this second wavelength (Ab).

Thus, in FIG. 1, Aa is the absorbance of compound A at wavelength $\lambda_a$; Ab is the absorbance of compound A at wavelength $\lambda_b$; Ba is the absorbance of compound B at wavelength $\lambda_a$; and Bb is the absorbance of compound B at wavelength $\lambda_b$. Accordingly, the total absorbance measured at wavelength $\lambda_a$ is the sum of the absorbances of compounds A and B at wavelength $\lambda_a$ (Aa'=Aa+Ba). Similarly, the total absorbance measured at wavelength $\lambda_b$ is the sum of the absorbances of compounds A and B at wavelength $\lambda_b$ (Bb'=Bb+Ab). Thus, in order to correct for the interference of compound B at wavelength $\lambda_a$, the following formula is used: (II) Aa=Aa'-Ba. Substituting for Ba, formula (III) is derived: Aa=Aa'-Ba or Aa=Aa'-k·Bb. In formula (III) by substituting for Bb with (Bb'-Ab), formula (IV) is derived: Aa=Aa' -k·(Bb'-Ab), which is the same as formula (V): Aa=Aa'-k·Bb'+k·Ab, where k is a constant and represents the ratio between Bb and Ba, and Bb' can be measured. Ab, however, cannot be measured directly because it is buried under Bb. Accordingly, Aa' cannot be corrected. There is, however, always a constant ratio between Aa and Ab just as there is always a ratio between Bb and Ba (although the ratios between Aa and Ab and Bb and Ba are not necessarily the same). Thus, Ab=c·Aa which can be substituted into formulae (V) to yield the following equation: (VI) Aa=Aa'-k·Bb'+k·c·Aa which can be rearranged to formula (VII) Aa=(Aa'-k·Bb')/(1-k·c). With formula (VII), Ab does not have to be measured so that a true absorbance of compound A at wavelength $\lambda_a$ can be obtained.

The present invention is based on the observation that the signal producing composition is able to produce a measurable response having a characteristic ratio of signals at two different wavelengths. This characteristic ratio of signals at two different wavelengths is the basis for the existence of the constants k and c, respectively, and for the ability of the present method to detect and/or quantitate analytes in multi-component systems.

Thus, by taking a second absorbance measurement, one is able to correct for the absorbance of the interfering or contaminating materials. In this way, an accurate measure is obtained for the concentration of an analyte in a particular system. Accordingly, this method allows for the quick and accurate detection and/or quantification of an analyte in a multi-component medium that is independent of the wavelength at which the absorbance of a chromophore produced when a chromogen reacts with an analyte of interest.

Figure 2:
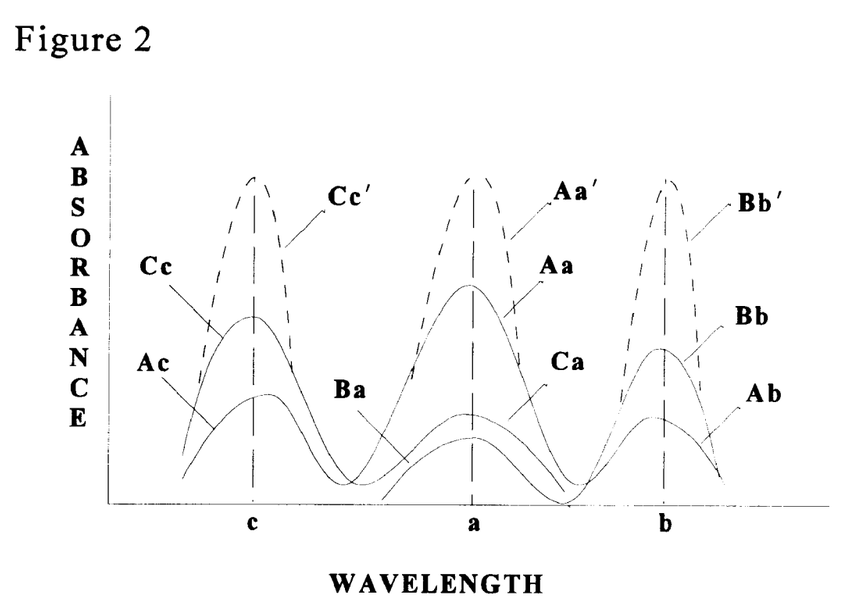
FIG. 2 depicts the absorbance of three compounds at three wavelengths according to the present invention.

Moreover, as set forth above and further illustrated in FIG. 2, the present method also allows for the detection of three or more analytes in a multi-component medium as long as the number of stimuli used are equal to or greater than the sum of the analytes or interfering components in the multi-component medium.

Thus, in FIG. 2, the present method is able to detect and/or quantitate the presence of an analyte when multiple analytes or interfering components, i.e., three or more, mask the signal produced by the analyte of interest because the correction of the interfering signals Ba and Ca can be accomplished by measuring Bb' and Cc' at two different wave lengths. Such corrections are made using Formula I above as shown in the following derivation:

Aa=Aa'-Ba-Ca

=Aa'-kb·Bb-kc·Cc

=Aa'-kb(Bb'-Ab)-kc(Cc'-Ac)

=Aa'-kb·Bb'+kb·Ab-kc·Cc'+kc·Ac

=Aa'-kb·Bb'+kb·kd·Aa-kc·Cc'+kc·ke·Aa

Rearrange, (1 -kb·kd-kc·ke)Aa

=Aa'-kb·Bb'-kc·Cc'

Aa=(Aa'-kb·Bb'-kc·Cc')/(1-kb·kd-kc·ke)

Thus, the present method is effective at determining the presence and/or quantity of an analyte in a sample provided that there are no interfering components overlapping at a stimulus, i.e., $\lambda_b$ or $\lambda_c$, that must be used for corrections.

This method is able to both detect the presence of and/or quantitate the amount of an analyte in the multi-component medium of the present invention. For example, an analyte's presence may be detected with a percent coefficient of variance of about 30% to about 50%. Furthermore, an analyte can be quantified, i.e., its concentration may be determined, with a percent coefficient of variance of about 3% to about 7%. The coefficient of variance with respect to the detection and/or quantitation of any particular analyte will, of course, vary depending upon the measuring devices and reagents used.

In the present invention, the stimulus or stimuli used to excite the multi-component medium can be derived from any source provided that such stimuli are able to induce the signal producing molecule to produce a detectable signal. Such stimuli may include for example, radiation from the electromagnetic spectrum, current, nuclear magnetic resonance, voltage, fluorescence, radioactivity and temperature.

As described above with reference to FIGS. 1 and 2, multiple signals may be detected by exciting or stimulating the multi-component medium at more than one point, such as for example, at more than one excitation wavelength and subsequently measuring the corresponding absorbencies at at least first and second wavelengths $\lambda_a$ and $\lambda_b$ (labeled a and b in FIGS. 1 and 2). As set forth previously, the number of signals to be detected will be determined with reference to the number of stimuli provided and the number of analytes and interfering substances for which corrections must be made. In a preferred embodiment of the present invention, for example, $\lambda_a$ and $\lambda_b$ are 630 nm and 700 nm, respectively.

Figure 3:
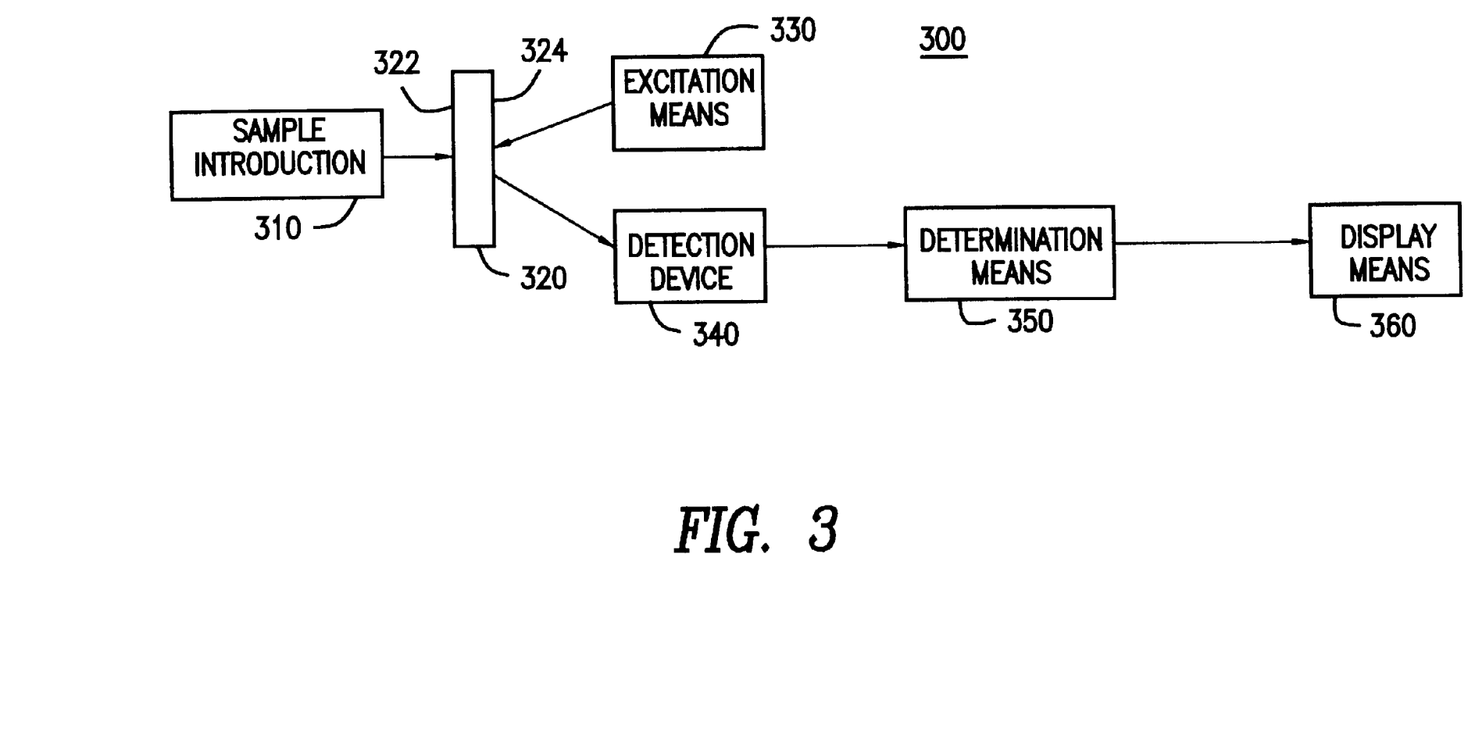
FIG. 3 is a functional depiction of the analyte detection system of the present invention.

In another embodiment of the present invention, an analyte detection system FIG. 3 is provided for determining the presence and/or concentration of glucose in a blood sample which is in contact with a porous substrate 320 having a blood application 322 and an analyte detection surface 324. In this system for detecting glucose in a blood sample, the presence and/or quantity of glucose cannot be directly determined because of the presence of at least one interfering signal generated by the hemoglobin in the red blood cells of the blood sample.

The porous substrate 320 of this embodiment includes a matrix of a hydrophilic polymer with pores dispersed throughout the matrix. These pores are in communication with both the blood application 322 and analyte detection surface 324. Moreover, the diameter of the pores are sufficiently large to allow red blood cells in the blood sample to freely migrate between the blood application surface 322 and the analyte detection surface 324.

In this system, a blood sample is introduced is a sample introduction 310 onto a blood application surface 322 as set forth above. To work, the present system only requires a drop of blood from a patient. The volume of such a drop of blood can range from about 10 µl to about 100 µl. The blood application surface 322 of the present system can be any porous surface 322 which is adapted to receive blood. This surface, however, must be adapted to allow red blood cells to freely migrate between the blood application surface 324 and the analyte detection surface 324 via the pores in the hydrophilic matrix of the substrate 320. Accordingly, the blood application surface 322 is in fluid contact with the analyte detection surface 324 so that glucose, as well as other analytes, are not hindered in the movement to the analyte detection surface 324 .

The analyte detection surface 322 of the present invention contains a glucose specific reagent and an indicator, although other reagents and indicators may be substituted therefor to detect analytes different from glucose. The reagent and indicator may be disposed on the analyte detection surface 322 itself or may be impregnated within the pores of the polymer matrix. The only limitation as to how the reagent and indicator are arranged on the analyte detection surface 324 is that they must be accessible to react with the analytes, i.e., glucose, contained within the blood sample.

When the blood sample reaches the analyte detection surface 324 of the present invention, a signal producing composition is formed through the reaction of the glucose-specific reagent, the indicator and the analyte, i.e., glucose, in the blood sample as described in detail above. The detection of any signals produced from this reaction, as well as the determination of the presence and/or quantity of glucose in a blood sample has been described above with reference to FIGS. 1 and 2.

The presence and/or concentration of glucose in the blood sample can be determined as previously set forth. Furthermore, one or more signals can be detected by stimulating or exciting the blood sample and taking measurements as described hereinabove. Moreover, Formula I, as set forth above, is used in the present system for determining the presence and/or concentration of glucose, or any other analyte compatible with the present invention.

As set forth above, it is preferred that $\lambda_a$ and $\lambda_b$ described in Formula I are 630 nm and 700 nm, respectively. Other wavelengths, however, are also contemplated by the present invention depending upon the analyte to be detected, the sample, and the reagent and indicators used.

In the present system, the signal producing composition, as set forth above, may produce a measurable response having a characteristic ratio of signals at two different wavelengths. Furthermore, this ratio is the basis for the existence of constants k and c, respectively. Also as set forth above, a signal is produced by the signal producing composition which includes absorbance, voltage, radioactivity, temperature, current and fluorescence. The glucose-specific reagent may include a chromogen, such as for example 3,3',5,5'-Tetramethylbenzidine; a Trinder reagent; or any other substance capable of producing a signal detectable by the present system.

In another embodiment of the present invention, a process for detecting one or more analytes in a multi-component system is provided in which the ability to directly detect the analytes is masked by no more than one interfering component of the system. This process includes forming a signal producing composition by reacting an analyte with a reagent, as set forth above. The process further includes exciting the system with more than one stimulus to produce signals from the signal producing composition, as previously described. The signal or signals are then measured and the presence and/or concentration of one or more of the analytes is determined according to the method set forth above.

In a further embodiment of the present invention, a detection device 340 is provided for detecting the presence and/or concentration of one or more analytes in a blood sample when the analyte cannot be directly detected. This device 300 includes the hydrophilic porous substrate 320 with the blood application surface 322 and the analyte detection surface 324 which are described in more detail above.

An analyte-specific reagent and an indicator as described in more detail above are dispersed on the analyte detection surface for reacting with the analyte to produce a signal producing composition. When excited, this signal producing composition produces at least two signals at wavelengths ($\lambda_a$) and ($\lambda_b$), respectively. The number of signals produced, however, must be equal to or greater than the sum of the number of the analytes in the blood sample and any interfering components therein, provided that the signals are different than a signal for measuring the analyte.

The device 300 also includes excitation means 330 for exciting the sample on the analyte detection surface 324. Moreover, detection means 340 are also provided for detecting at least two signals. The excitation means 330 and detection means 340 can include spectrophotometers, fluorescent spectrophotometer, voltage detectors, etc. as previously set forth. It is within the knowledge of one skilled in the art to select appropriate excitation and detection means based on the analyte to be detected and the detection reagents used.

The device 300 further includes a determination means 350 for determining the presence and/or concentration of the analyte by applying mathematical formulas to at least the first and second signals. The formulas are defined in Formula I above. A display means 360 is also provided for displaying the presence and/or concentration of the analyte. Such display means 360 can be, for example, in the form of a monitor, a computer printout including tables of data and graphical representations, a strip of material which visually cues an observer as to the presence and/or concentration of a particular analyte and the like. Such display means are well known in the art and may be selected by the skilled artisan with reference to the intended application.

The following examples are set forth to illustrate the methods of the present invention. These examples are provided for purposes of illustration only and are not intended to be limiting in any sense.

EXAMPLE 1A

Preparation of a Substrate to be Coated

A test strip according to the present invention was prepared as follows: a piece of nylon membrane (Magna, 1.2pm from Micron Separations, Inc. Westborough, Mass.) was impregnated by dipping in a 1% of DOSS solution (0.2 gm Dioctyl sulfosuccinate sodium salt in 20 gm distilled water). The nylon membrane was then suspended and allowed to dry at 65° C. for 15 minutes in an oven.

EXAMPLE 1B

Preparation of An Analyte Detection Composition According to the Present Invention An analyte detection composition, Composition A was prepared as follows: 0.6 g of microcrystalline cellulose particles was added to 12.5 g of distilled water, and stirred for 30 minutes. To 3 g of the cellulose particle solution was added 0.6 ml of 0.5 M phosphate buffer (pH 5.0). This composition was stirred for about 20 minutes. The following reagents were then added to this composition: 2.5 g of hydroxyethyl cellulose ($7.2 \times 10^5$ M.W.) solution (0.96 g of hydroxyethyl celluose in 36 g of 0.5 M phosphate buffer (pH 5), which was stirred overnight); 2.6 g of a vinyl acetate-ethylene copolymer (Airflex 300 from Air Products & Chemicals, Inc., Allentown, Pa.); 0.4 ml of Igepal CO-530 (prepared by mixing 0.2 g of Igepal CO-530 with 1.65 g of distilled water); and 0.4 ml of semicarbazide solution (0.1 g of semicarbazide dissolved in 1 g of distilled water). The resulting mixture was stirred for about 20 minutes. Then, 0.3 ml of a $CaCl_2$ solution (1.4704 g of $CaCl_2 \cdot 2H_2O$ dissolved in 10 g of distilled water) was slowly added to the above-described composition with constant stirring for about 15 minutes. 0.1 ml of a BHT solution (prepared by adding 0.1 g of 2,6-di-tert-butyl-p-cresol dissolved in 0.765 g of acetone), 0.67 ml of TMB solution (0.14 g of 3,3',5,5'-tetramethylbenzidine and 0.14 g of dioctyl sulfosuccinate sodium salt dissolved in 0.8 g of acetone), 0.5 ml of 4-sulfobenzoate solution (2.4 g of 4-sulfobenzoic acid, potassium salt was mixed with 10 g of distilled water, and the pH of the solution was adjusted to 5.0 with 1.75 ml of a 10 N NaOH solution. This solution was then filtered through filter paper) and 0.84 ml of enzyme solution in that order, were slowly added to this composition. The enzyme solution was prepared with 5232$\mu$ glucose oxidase, 13397$\mu$ horseradish peroxidase, 0.2 g of Crotein spc (Croda Inc. N.J.) and 0.6 g of distilled water which were stirred and mixed well.

EXAMPLE 1C

Coating a Substrate with an Analyte Detection Composition of the Present Invention On a glass plate, Composition A of Example 2 was applied onto the dried nylon membrane of Example 1 to a wet thickness of 6.4 ml with a glass rod whose two ends were taped to afford the desired wet coating thickness. The glass plate with the coated membrane on it was dried in an oven at 65° C. for 15 minutes.

EXAMPLE 1D

Comparison of Prior Art Glucose Test Strip and Test Strips of Present Invention

The coated substrate of Example was 1C cut into test strips which are compatible with commercially available glucose meters, such as, One Touch™ II or Basic glucose meters.

The spiked blood samples with various hematocrit levels were applied to the test strips of the present invention (runs 1–8), as well as to a prior art glucose test strip. The test strips were then placed in One Touch™ glucose meters and the glucose concentrations were detected. The results of these tests are indicated in Table I below:

TABLE I

|  | Sample 1** mg/dL Glucose 42% Hematocrit | Sample 2 mg/dL Glucose 52% Hematocrit | Sample 3** mg/dL Glucose 42% Hematocrit | Sample 4 mg/dL Glucose 52% Hematocrit | Sample 5** mg/dL Glucose 42% Hematocrit | Sample 6 mg/dL Glucose 52% Hematocrit |
| --- | --- | --- | --- | --- | --- | --- |
| Prior Art Strip | 85 | 77 | 157 | 145 | 454 | 427 |
| run 1 | 90 | 83 | 223 | 174 | 533 | 510 |
| run 2 | 90 | 84 | 186 | 191 | 545 | 531 |

TABLE I-continued

|  | Sample 1** mg/dL Glucose 42% Hematocrit | Sample 2 mg/dL Glucose 52% Hematocrit | Sample 3** mg/dL Glucose 42% Hematocrit | Sample 4 mg/dL Glucose 52% Hematocrit | Sample 5** mg/dL Glucose 42% Hematocrit | Sample 6 mg/dL Glucose 52% Hematocrit |
|---|---|---|---|---|---|---|
| run 3 | 94 | 74 | 232 | 182 | 578 | 527 |
| run 4 | 85 | 84 | 196 | 213 | 516 | 513 |
| run 5 |  |  | 205 | 175 | 525 | 545 |
| run 6 |  |  | 213 | 196 | 556 | 502 |
| run 7 |  |  | 208 | 188 | 541 | 523 |
| run 8 |  |  | 211 | 201 | 542 | 517 |
| Ave. | 89.75 | 81.25 | 209.25 | 190 | 542 | 521 |
| Norm* | 89.75 | 89.69 | 209.25 | 205.72 | 542 | 553.94 |

**Samples 2, 4, and 6 of higher hematocrit were prepared from Samples 1, 3, and 5 of lower hematocrit by removing plasma therefrom.
*Strip values of the higher 52% hematocrit samples were normalized by multiplying by a certain correction factor: (One Touch value of 42% hematocrit sample which was used to prepare the 52% hematocrit sample / value of 52% hematocrit sample). Thus, the normalized values of the higher hematocrit samples can be compared easily with those of the lower hematocrit levels.

These results indicate that the test strips of the present invention are able to determine the level of glucose present over a wide range of concentrations. Furthermore, the results indicate that interference due to higher hematocrit levels can be easily compensated for using One Touch™ glucose meters.

EXAMPLE 2A

Determination of Glucose Concentration in a Blood Sample Using a Trinder Reagent A nylon membrane as described in Example 1A was coated with a Trinder reagent and with Composition B of the present invention using the same process set forth in Example 1C. Composition B was prepared by combining the following reagents: 0.6 g 2,5-Furandione, polymer with methoxyethene solution (prepared by adding 6 g of Gantrez AN-169 (ISP Technologies, Inc., Wayne, N.J.) to 72 g of distilled water, and stirring at 80° C. for two hours until the solution became clear. The solution was adjusted to pH 4.0 with 3.2 ml of 10 N NaOH solution); 1 g of a DOSS solution (The DOSS solution was prepared by mixing 0.65 g of dioctyl sulfosuccinate sodium salt and 5 ml of distilled water for 30 minutes.); 0.7 ml of 4-sulfobenzoate solution (This solution was prepared by adding 2.4027 g of 4-sulfobenzoic acid, potassium salt to 10 g of distilled water with stirring while 1.75 ml of 10 N NaOH was added to adjust the pH to 5.0. This solution was then filtered through filter paper.); 0.8 ml of Igepal CO-530 (prepared by mixing 0.03 g of a surfactant (Igepal CO-530) with 1 g of distilled water); 0.3 ml of semicarbazide (0.1 g semicarbazide dissolved in 1 g of distilled water); 1 ml of phosphate buffer (pH 5); 0.3 ml of $CaCl_2$ (containing 1.4704 g of $CaCl_2 \cdot 2H_2O$ dissolved in 10 g of distilled water); and 2.375 ml of distilled water. These reagents were stirred for 30 minutes. Then, 0.84 ml of an enzyme solution was added and the composition was stirred for an additional 20 minutes. The enzyme solution was prepared with 1949 $\mu$ glucose oxidase, 1935 $\mu$ horseradish peroxidase, 0.2 g of Crotein spc (Croda Inc. N.J.) and 0.6 g of distilled water which were stirred and mixed well.

The Trinder reagent was prepared by adding 1 g of the 2,5 Furandione, polymer with methoxyethene (Gantrez An-169 solution) to 9 g of distilled water, and adjusting the pH to 7.0 with 10 N NaOH solution while the solution was stirred. To 0.2 g of this Gantrez solution was added 24.6 mg of N-ethyl-N-(2-hydroxy-3-sulfopropyl)-3,5-dimethylaniline, sodium salt, monohydrate (MAOS), 15.2 mg of 4-aminoantipyrine, 0.6 g of distilled water. The solution was stirred to dissolve. Then 1.1 ml of ethanol was slowly added while stirring.

EXAMPLE 2B

Comparison of Prior Art Glucose Test Strip and Test Strip of Present Invention

Using composition B and the Trinder reagent solution and the nylon substrate described in Example 2A, the procedure set forth in Example 1 D was repeated. The results of the glucose determinations are set forth below in Table II.

TABLE II

|  | Sample 1** mg/dL Glucose 42% Hematocrit | Sample 2 mg/dL Glucose 52% Hematocrit | Sample 3** mg/dL Glucose 42% Hematocrit | Sample 4 mg/dL Glucose 52% Hematocrit | Sample 5** mg/dL Glucose 42% Hematocrit | Sample 6 mg/dL Glucose 52% Hematocrit |
|---|---|---|---|---|---|---|
| Prior Art Strip | 87 | 81 | 162 | 146 | 462 | 423 |
| run 1 | 75 | 66 | 125 | 114 | 346 | 312 |
| run 2 | 71 | 68 | 128 | 116 | 358 | 326 |
| run 3 | 74 | 65 | 127 | 113 | 335 | 322 |
| run 4 | 72 | 69 | 126 | 117 | 369 | 316 |
| Ave. | 73 | 67 | 126.5 | 115 | 352 | 319 |
| Norm.* | 73 | 71.96 | 126.5 | 127.6 | 352 | 348.41 |

**Samples 2, 4, and 6 of higher hematocrit were prepared from Samples 1, 3, and 5 of lower hematocrit by removing plasma therefrom.

TABLE II-continued

| | Sample 1** mg/dL Glucose 42% Hematocrit | Sample 2 mg/dL Glucose 52% Hematocrit | Sample 3** mg/dL Glucose 42% Hematocrit | Sample 4 mg/dL Glucose 52% Hematocrit | Sample 5** mg/dL Glucose 42% Hematocrit | Sample 6 mg/dL Glucose 52% Hematocrit |
|---|---|---|---|---|---|---|

*Strip values of higher 52% hematocrit sample were normalized by multiplying by a certain correction factor (One Touch value of 42% hematocrit sample which was used to prepare the 52% hematocrit sample / value of 52% hematocrit sample). Thus, the normalized values of the samples can be compared easily with those of the lower hematocrit levels.

These results indicate that test strips of the present invention are able to determine the levels of glucose present over a wide range of concentrations. Furthermore, the results indicate that interference due to higher hematocrit levels can be easily compensated for using One Touch™ glucose meters.

EXAMPLE 3A

Coating A Substrate With an Analyte Detection Composition of the Present Invention On a glass plate, a Trinder reagent solution was coated onto a piece of nylon membrane (Biodyne B, 5 μm from Pall Biosupport Division, East Hills, N.Y.) to a wet thickness of 6.2 ml as described in Example 1C. The coated membrane was then dried in an oven at 65° C. for 20 minutes. Composition C as described in further detail below was then applied to the coated membrane in the same fashion as set forth in Example 1C.

Composition C was prepared by combining the following reagents: 2.4 g of a solution containing 2,5 Furandione, polymer with methoxyethene (6 g of Gantrez AN-169 in 72 g of distilled water which was stirred and heated to 80° C. for two hours until it became a clear solution. Then, the solution was adjusted to pH 4.0 by 3.2 ml of 10 N NaOH solution.); 1.0 ml of 0.5 M phosphate buffer (pH 5.0); 0.65 g of DOSS solution (prepared by adding 0.65 g of dioctyl sulfosuccinate sodium salt to 5 ml of distilled water for 30 minutes.); 1 g of Airflex 300; 0.8 ml of Igepal CO-530 solution (prepared by mixing 0.03 g of a surfactant Igepal CO-530 with 1 g of distilled water); 0.4 ml of semicarbazide solution (0.1 g of semicarbazide was dissolved in 1 g of distilled water); 0.3 ml of $CaCl_2$ solution (1.4704 g of $CaCl_2 \cdot 2H_2O$ dissolved in 10 g of distilled water); 0.7 ml of 4-sulfobenzoate solution (prepared by adding 2.4027 g of 4-sulfobenzoic acid, potassium salt to 10 g of distilled water. This solution was stirred while 1.75 ml of 10 N NaOH was used to adjust the pH to 5.0. The solution was then filtered through filter paper.); and 2.375 ml of distilled water. The solution was stirred for 30 minutes. Then, 0.84 ml of enzyme solution was added and stirred for 15 minutes. This enzyme solution was prepared with 2225 μ of glucose oxidase, 1918 μ of horseradish peroxidase, 0.2 g of Crotein spc (Croda Inc. N.J.) dissolved in 0.6 g of distilled water.

Trinder reagent solution: To 1 g of 2,5 Furandione, polymer with methoxyethene (Gantrez An-169 solution) was added 9 g of distilled water, and the pH was adjusted to 7.0 with 10 N NaOH solution while the solution was stirred. To 0.2 g of this Gantrez solution was added 28.7 mg of N-ethyl-N-(3-sulfopropyl)-3,5-dimethylaniline, sodium salt, monohydrate (MAPS), 7.1 mg of 4-aminoantipyrine, 0.6 g of distilled water. The solution was stirred to dissolve. Then 1.1 ml of ethanol was added drop by drop while stirring.

EXAMPLE 3B

Comparison of Prior Art Glucose Test Strip and Test Strip of the Present Invention Using Composition C, Trinder reagent solution and the substrate described in Example 3A, the procedure set forth in Example 1D was repeated. The results of the glucose determinations are set forth below in Table III.

TABLE III

| | Sample 1** mg/dL Glucose 42% Hematocrit | Sample 2 mg/dL Glucose 52% Hematocrit | Sample 3** mg/dL Glucose 42% Hematocrit | Sample 4 mg/dL Glucose 52% Hematocrit | Sample 5** mg/dL Glucose 42% Hematocrit | Sample 6 mg/dL Glucose 52% Hematocrit |
|---|---|---|---|---|---|---|
| Prior Art Strip | 85 | 81 | 164 | 154 | 456 | 433 |
| run 1 | 106 | 98 | 146 | 137 | 402 | 382 |
| run 2 | 110 | 102 | 150 | 141 | 409 | 465 |
| run 3 | 107 | 92 | 145 | 143 | 383 | 387 |
| run 4 | 109 | 97 | 151 | 139 | 394 | 400 |
| Ave. | 108 | 97.5 | 148 | 140 | 397 | 393.5 |
| Norm* | 108 | 102.05 | 148 | 149.09 | 397 | 414.4 |

**Samples 2, 4, and 6 of higher hematocrit were prepared from Samples 1, 3, and 5 of lower hematocrit by removing plasma therefrom.
*Strip values of 51% hematocrit sample were normalized by multiplying by a certain correction factor (One Touch value of 41% hematocrit sample which was used to prepare the 51% hematocrit sample / value of 51% hematocrit sample). Thus, the normalized values of the higher hematocrit samples can be compared easily with those of the lower hematocrit samples.

These results indicate that test strips of the present invention are able to determine the levels of glucose present over a wide range of concentrations. Furthermore, the results indicate that interference due to higher hematocrit levels can be easily compensated for using One Touch™ glucose meters.

In the present example, the oxidized TMB, MAOS and MAP products (the chromophores) all absorb substantially at both 635 nm and 700 nm. Thus, the present invention can be used to detect analytes, i.e., glucose, using such chromophores.

The invention being thus described, it will be obvious that the same may be varied in many ways. Such variations are not to be regarded as a departure from the spirit and scope of the invention and, all such modifications are intended to be included within the scope of the following claims.

What is claimed is:

1. An analyte detection system for determining the presence and/or concentration of glucose in a blood sample having two or more interfering components masking the presence and/or concentration of glucose in contact with a substrate having a blood application surface and an analyte detection surface wherein the presence and/or concentration of glucose cannot be directly determined comprising:
   a) means for introducing said blood sample onto said blood application surface;
   b) means for allowing said sample to migrate through said porous substrate to said analyte detection surface, wherein said detection surface includes a glucose-specific reagent and an indicator disposed thereon;
   c) means for forming a signal producing composition through the reaction of said glucose-specific reagent, said indicator and said glucose present in said blood sample;
   d) means for stimulating said sample with one or more stimuli;
   e) means for detecting one or more signals produced in response to d, and for correcting for any interfering signals produced by other analytes and/or two or more interfering components, wherein the number of stimuli required is equal to or greater than the sum of the number of analytes in said sample and any interfering components therein, provided that said stimuli for said interfering components are different from a stimulus for measuring said glucose and the interfering components must not simultaneously overlap at at least one correction point and further provided that said signal producing composition produces a measurable response having a characteristic ratio of signals at two different stimuli; and
   f) means for determining the presence and/or concentration of said glucose by applying a mathematical formula to said one or more signals.

2. The system of claim 1, wherein said porous substrate further comprises a matrix of a hydrophilic polymer, said polymer having pores dispersed throughout said matrix and in communication with said blood application and analyte detection surfaces, wherein the diameter of said pores is sufficiently large to allow at least a portion of said sample to freely migrate therebetween.

3. The system according to claim 1, wherein the presence of glucose in said blood sample is detected with a percent coefficient of variance between about 30% to about 50%.

4. The system according to claim 1, wherein the concentration of glucose in said blood sample is detected with a percent coefficient of variance of about 3% to about 7%.

5. The system according to claim 1, wherein said one or more signals are detected by exciting said blood sample at at least three excitation wavelengths and measuring its absorbance produced at said at least three wavelengths $\lambda_a$, $\lambda_b$ and $\lambda_c$, respectively.

6. The system according to claim 5, wherein said presence and/or concentration of glucose is proportional to the magnitude of a signal produced by said glucose (Aa) and is determined according to mathematical formula I:

Concentration and/or Presence of Glucose=E·Aa wherein Aa=(Aa'−kb·Bb'−kc·Cc')/(1−kb·kd−kc·ke) and Aa is said true value for said analyte, Aa' is a measurable signal produced at $\lambda_a$ in response to a single stimulus by said signal producing composition (Aa) and said no more than two interfering components (Ba and Ca) Bb' is a measurable signal produced at $\lambda_b$ in response to said stimulus by said signal producing composition (Ab) and said no more than one interfering component (Bb), Cc' is a measurable signal produced at $\lambda_c$ in response to said stimulus by said signal producing composition (Ac) and said no more than one interfering component (Cc), kb is a constant and is a ratio between Ba and Bb, kc is a constant and is a ratio between Ca and Cc, kd is a constant and is a ratio between Ab and Aa, and ke is a constant and is a ratio between Ac and Aa.

7. The system according to claim 5, wherein $\lambda_a$ is about 630 nm and $\lambda_b$ is about 700 nm.

8. The system according to claim 1, wherein said signal producing composition produces a signal selected from the group consisting of absorbance, voltage, radioactivity, temperature, current, fluorescence and mixtures thereof.

9. The system according claim 1, wherein said glucose-specific reagent includes a chromogen.

10. The system according to claim 9, wherein said chromogen is 3,3',5,5'-Tetramethylbenzidine.

11. The system according to claim 1, wherein said glucose-specific reagent is a Trinder reagent.

12. A process for detecting one or more analytes in a multi-component system wherein the ability to directly detect said one or more analytes in a signal producing composition is masked by two or more interfering components of said multi-component system comprising:
   a) exciting said system with one or more stimuli to produce an interference-correction signal from said signal producing composition, whereby the number of stimuli provided is equal to or greater than the sum of the number of said analytes in said multi-component medium and any interfering components therein, provided that said stimuli for said interfering components are different from a stimulus for measuring said analyte, and the interfering components must not overlap at least one interfering correction stimulus that is used for said corrections;
   b) measuring said signal or signals at detection points; and
   c) determining the presence and/or concentration of said one or more analytes by applying a correction to said signal or signals, wherein said signal or signals are proportional to said analyte or analytes to be detected said correction being:

Concentration and/or Presence of Analyte=E·Aa wherein Aa=(Aa'−kb·Bb'−kc·Cc')/(1−kb·kd−kc·ke) and Aa is said true value for said analyte, Aa' is a measurable signal produced in response to a single stimulus by said signal producing composition (Aa) and said no more than two interfering components (Ba and Ca) at said first detection point, Bb' is a measurable signal produced in response to said stimulus by said signal producing composition (Ab) and said no more than one interfering component (Bb) at said second detection point, Cc' is a measurable signal produced in response to said stimulus by said signal producing composition (Ac) and said no more than one interfering component (Cc) at said third detection point, kb is a constant and is a ratio between Ba and Bb, kc is a constant and is a ratio between Ca and Cc, kd is a constant and is a ratio between Ab and Aa, and ke is a constant and is a ratio between Ac and Aa.

13. The process of claim 12 further including a step of forming said signal producing composition by reacting an analyte with a reagent.

14. The process according to claim 13 wherein said analyte's presence is detected with a percent coefficient of variance between about 30% to about 50%.

15. The process according to claim 12 wherein said analyte's concentration is detected with a percent coefficient of variance of about 3% to about 7%.

16. The process according to claim 12, wherein said signal producing composition produces a measurable response having a characteristic ratio of signals at two different stimuli.

17. The process according to claim 12 wherein said signal producing composition produces a signal selected from the group consisting of absorbance, voltage, radioactivity, temperature, current and fluorescence.

18. The process according claim 12, wherein said analyte is glucose and said reagent is a glucose-specific reagent.

19. The process according to claim 18, wherein said glucose-specific reagent is a chromogen.

20. The process according to claim 19, wherein said chromogen is 3,3',5,5'-Tetramethylbenzidine.

21. The process according to claim 12, wherein said signal producing composition is a Trinder reagent.

22. A device for detecting the presence and/or concentration of one or more analytes in a blood sample when said analyte cannot be directly detected comprising:
   a) a hydrophilic porous substrate with a blood application surface and an analyte detection surface, said substrate comprising a polymeric matrix having pores dispersed throughout said matrix and in communication with said blood application and analyte detection surfaces, wherein the diameter of said pores is sufficiently large to allow at least a portion of said sample to freely migrate therebetween;
   b) an analyte-specific reagent and an indicator dispersed on said analyte detection surface for reacting with said analyte to produce a signal producing composition which, when excited, produces at least three signals at wavelengths ($\lambda_a$), ($\lambda_b$) and ($\lambda_c$), respectively to correct for any interfering signal or signals produced by other analytes or interfering components in said sample;
   c) excitation means for exciting said sample on said analyte detection surface;
   d) detection means for detecting said at least three signals, whereby the number of signals produced must be equal to or greater than the sum of the number of said analytes in said blood sample and any interfering components therein, provided that said signals for said interfering compounds are different from a signal for measuring said analyte, and the interfering components must not overlap at at least one interfering correction stimulus that is used for said corrections and further provided that said signal producing composition produces a measurable response having a characteristic ratio of signals at the two different wavelengths;
   e) means for determining the presence and/or concentration of said analyte by applying said corrections to said at least first and second signals, said corrections being:

Concentration and/or Presence of Glucose=E·Aa wherein Aa=(Aa'-kb·Bb'-kc·Cc')/(1-kb·kd-kc·ke) and Aa is said true value for said analyte, Aa' is a measurable signal produced $\lambda_a$, in response to a single stimulus by said signal producing composition (Aa) and said no more than two interfering components (Ba and Ca), Bb' is a measurable signal produced at $\lambda_b$ in response to said stimulus by said signal producing composition (Ab) and said no more than one interfering component (Bb), Cc' is a measurable signal produced at $\lambda_c$ in response to said stimulus by said signal producing composition (Ac) and said no more than one interfering component (Cc), kb is a constant and is a ratio between Ba and Bb, kc is a constant and is a ratio between Ca and Cc, kd is a constant and is a ratio between Ab and Aa, and ke is a constant and is a ratio between Ac and Aa and;
   f) display means for displaying said presence and/or concentration of said analyte.

23. A method for determining the presence and/or concentration of glucose in a blood sample in contact with a porous substrate having a blood application surface and an analyte detection surface wherein the presence and/or concentration of glucose cannot be directly determined comprising:
   a) introducing said blood sample onto said blood application surface;
   b) allowing a portion of said sample to migrate through said porous substrate to said analyte detection surface, wherein said detection surface includes a glucose-specific reagent and an indicator disposed thereon;
   c) forming a signal producing composition through the reaction of said glucose-specific reagent, said indicator and said glucose present in said blood sample;
   d) stimulating said sample with one or more stimuli;
   e) detecting one or more signals produced in response to d, and for correcting for at least two or more interfering signals produced by other analytes and/or interfering components, wherein the number of stimuli required is equal to or greater than the sum of the number of analytes in said sample and any interfering components therein, provided that said stimuli for said interfering compounds are different from a stimulus for measuring said glucose and the interfering components must not overlap at at least one interfering correction stimulus that is used for said corrections and further provided that said signal producing composition produces a measurable response having a characteristic ratio of signals at two different stimuli; and
   f) determining the presence and/or concentration of said glucose by applying said corrections based on said characteristic ratio to said one or more signals.

24. The method of claim 23, wherein said porous substrate further comprises a matrix of a hydrophilic polymer, said polymer having pores dispersed throughout said matrix and in communication with said blood application and analyte detection surfaces, wherein the diameter of said pores is sufficiently large to said portion of said blood sample to freely migrate therebetween.

25. The method according to claim 24, wherein the presence of glucose in said blood sample is detected with a percent coefficient of variance between about 30% to about 50%.

26. The method according to claim 24, wherein the concentration of glucose in said blood sample is detected with a percent coefficient of variance of about 3% to about 7%.

27. The method according to claim 24, wherein said one or more signals are detected by exciting said blood sample at least two excitation wavelengths and measuring its absorbance produced at said at least three wavelengths $\lambda_a$, $\lambda_b$ and $\lambda_c$, respectively.

28. The method according to claim 27, wherein said presence and/or concentration of glucose is proportional to the magnitude of a signal produced by said glucose (Aa) and is determined according to mathematical formula I:

Concentration and/or Presence of Glucose=E·Aa wherein $Aa=(Aa'-kb \cdot Bb'-kc \cdot Cc')/(1-kb \cdot kd-kc \cdot ke)$ and Aa is said true value for said analyte, Aa' is a measurable signal produced at $\lambda_a$, in response to a single stimulus by said signal producing composition (Aa) and said no more than two interfering components (Ba and Ca) Bb' is a measurable signal produced at $\lambda_b$ in response to said stimulus by said signal producing composition (Ab) and said no more than one interfering component (Bb), Cc' is a measurable signal produced at $\lambda_c$ in response to said stimulus by said signal producing composition (Ac) and said no more than one interfering component (Cc), kb is a constant and is a ratio between Ba and Bb, kc is a constant and is a ratio between Ca and Cc, kd is a constant and is a ratio between Ab and Aa, and ke is a constant and is a ratio between Ac and Aa.

29. The method according to claim 27, wherein $\lambda_a$ is about 630 nm and $\lambda_b$ is about 700 nm.

30. The method according to claim 24, wherein said signal producing composition produces a signal selected from the group consisting of absorbance, voltage, radioactivity, temperature, current, fluorescence and mixtures thereof.

31. The method according to claim 24, wherein said glucose-specific reagent includes a chromogen.

32. The method according to claim 31, wherein said chromogen is 3,3',5,5'-Tetramethylbenzidine.

33. The method according to claim 24, wherein said glucose-specific reagent is a Tinder reagent.

* * * * *